(12) United States Patent
Mault (10) Patent No.: US 7,291,114 B2
(45) Date of Patent: Nov. 6, 2007

(54) SYSTEM AND METHOD OF DETERMINING AN INDIVIDUALIZED DRUG ADMINISTRATION PROTOCOL

(75) Inventor: James R. Mault, Evergreen, CO (US)

(73) Assignee: Microlife Corporation, Taipei (TW)

( * ) Notice: Subject to any disclaimer, the term of this patent is extended or adjusted under 35 U.S.C. 154(b) by 722 days.

(21) Appl. No.: 10/404,838

(22) Filed: Apr. 1, 2003

(65) Prior Publication Data

US 2003/0220579 A1 Nov. 27, 2003

Related U.S. Application Data

(60) Provisional application No. 60/369,199, filed on Apr. 1, 2002.

(51) Int. Cl.
*A61B 5/08* (2006.01)
*A61B 10/00* (2006.01)
*G06F 17/00* (2006.01)

(52) U.S. Cl. .................. 600/531; 600/532; 600/529; 128/920

(58) Field of Classification Search ............... 600/300, 600/301, 529–543; 128/897–925
See application file for complete search history.

(56) References Cited

U.S. PATENT DOCUMENTS

| | | | |
|---|---|---|---|
| 2,630,798 A | 3/1953 | White et al. ............... 128/2.07 |
| 2,826,912 A | 3/1958 | Kritz ............................ 73/194 |
| 2,831,348 A | 4/1958 | Kritz ........................ 73/861.28 |
| 2,838,399 A | 6/1958 | Vogel, Jr. ........................ 99/48 |
| 2,869,357 A | 1/1959 | Kritz ............................. 73/32 |
| 2,911,825 A | 11/1959 | Kritz ............................ 73/194 |
| 2,920,012 A | 1/1960 | Sanders et al. ............ 167/51.5 |
| 3,212,684 A | 10/1965 | Seaton et al. ................ 73/190 |
| 3,220,255 A | 11/1965 | Scranton et al. ............... 73/204 |
| 3,250,270 A | 5/1966 | Bloom ....................... 128/2.07 |
| 3,306,283 A | 2/1967 | Arp ............................ 128/2.07 |
| 3,523,529 A | 8/1970 | Kissen ....................... 128/2.07 |
| 3,527,205 A | 9/1970 | Jones ......................... 128/2.08 |
| 3,681,197 A | 8/1972 | Smith ........................... 195/63 |
| 3,726,270 A | 4/1973 | Griffis et al. ............... 128/2.08 |
| 3,799,149 A | 3/1974 | Rummel et al. ........... 128/2.07 |
| 3,814,091 A | 6/1974 | Henkin ........................ 128/188 |
| 3,834,375 A | 9/1974 | Sanctuary et al. .......... 128/2.07 |
| 3,895,630 A | 7/1975 | Bachman ................... 128/2.07 |
| 3,938,551 A | 2/1976 | Henkin ........................ 137/613 |
| 3,962,917 A | 6/1976 | Terada .......................... 73/204 |
| 3,974,693 A | 8/1976 | Hardies ................... 73/861.28 |
| 3,979,480 A | 9/1976 | Radici et al. ............. 260/857 F |

(Continued)

*Primary Examiner*—Navin Natnithithadha
(74) *Attorney, Agent, or Firm*—Courtney Staniford & Gregory LLP (57) ABSTRACT

A system and method for determining an individualized drug dosage is provided. The system includes a metabolic rate sensing means for sensing the metabolic rate of the individual. The system also includes a computing device having a processor, a memory, an input device, and a display device. The system further includes a data storage means operatively in communication with the processor, and the data storage means includes a drug database containing drug dosage data. The method includes the steps of determining a standardized dosage for a drug. The method also includes the steps of measuring the actual metabolic rate of the individual and determining a metabolic comparison factor by comparing the measured actual metabolic rate to a predetermined standard metabolic rate. The method further includes the steps of adjusting the standardized drug dosage using the comparison factor.

31 Claims, 4 Drawing Sheets

U.S. PATENT DOCUMENTS

| | | | |
|---|---|---|---|
| 4,003,396 A | 1/1977 | Fleischmann | 137/83 |
| 4,051,847 A | 10/1977 | Henkin | 128/145.6 |
| 4,078,554 A | 3/1978 | Le Maitre et al. | 128/2.08 |
| 4,186,735 A | 2/1980 | Henneman et al. | 128/201.25 |
| 4,188,946 A | 2/1980 | Watson et al. | 128/204.22 |
| 4,197,857 A | 4/1980 | Osborn | 600/531 |
| 4,200,094 A | 4/1980 | Gedeon et al. | 128/201.13 |
| 4,211,239 A | 7/1980 | Raemer et al. | 128/716 |
| 4,221,224 A | 9/1980 | Clark | 128/718 |
| 4,230,108 A | 10/1980 | Young | 128/207.15 |
| 4,341,867 A | 7/1982 | Johansen | 435/189 |
| 4,359,057 A | 11/1982 | Manzella | 128/718 |
| 4,368,740 A | 1/1983 | Binder | 128/718 |
| 4,386,604 A | 6/1983 | Hershey | 128/718 |
| 4,425,805 A | 1/1984 | Ogura et al. | 73/861.29 |
| 4,440,177 A | 4/1984 | Anderson et al. | 600/532 |
| 4,444,201 A | 4/1984 | Itoh | 128/716 |
| 4,463,764 A | 8/1984 | Anderson et al. | 600/532 |
| 4,572,208 A | 2/1986 | Cutler et al. | 600/531 |
| 4,598,700 A | 7/1986 | Tamm | 128/671 |
| 4,608,995 A | 9/1986 | Linnarsson et al. | 128/713 |
| 4,619,269 A | 10/1986 | Cutler et al. | 128/719 |
| 4,648,396 A | 3/1987 | Raemer | 600/534 |
| 4,658,832 A | 4/1987 | Brugnoli | 600/532 |
| 4,719,923 A | 1/1988 | Hartwell et al. | 128/663 |
| 4,753,245 A | 6/1988 | Gedeon | 128/718 |
| 4,756,670 A | 7/1988 | Arai | 417/43 |
| 4,781,184 A | 11/1988 | Fife | 128/205.12 |
| 4,796,639 A | 1/1989 | Snow et al. | 600/532 |
| 4,850,371 A | 7/1989 | Broadhurst et al. | 600/532 |
| 4,856,531 A | 8/1989 | Merilainen | 600/532 |
| 4,909,259 A | 3/1990 | Tehrani | 600/531 |
| 4,914,959 A | 4/1990 | Mylvaganam et al. | 73/861.28 |
| 4,917,108 A | 4/1990 | Mault | 128/718 |
| 4,955,946 A | 9/1990 | Mount et al. | 600/532 |
| 4,986,268 A | 1/1991 | Tehrani | 128/204 |
| 4,998,018 A | 3/1991 | Kurahashi et al. | 250/343 |
| 5,022,406 A | 6/1991 | Tomlinson | 128/719 |
| 5,038,773 A | 8/1991 | Norlien et al. | 128/205.23 |
| 5,038,792 A | 8/1991 | Mault | 128/718 |
| 5,042,500 A | 8/1991 | Norlien et al. | 600/532 |
| 5,042,501 A | 8/1991 | Kenny et al. | 600/532 |
| 5,060,506 A | 10/1991 | Douglas | 73/24.1 |
| 5,060,655 A | 10/1991 | Rudolph | 128/716 |
| 5,060,656 A | 10/1991 | Howard | 128/718 |
| 5,069,220 A | 12/1991 | Casparie et al. | 128/719 |
| 5,072,737 A | 12/1991 | Goulding | 128/718 |
| 5,081,871 A | 1/1992 | Glaser | 73/863.23 |
| 5,095,900 A | 3/1992 | Fertig et al. | 128/207.14 |
| 5,095,913 A | 3/1992 | Yelderman et al. | 128/719 |
| 5,117,674 A | 6/1992 | Howard | 73/31.07 |
| 5,119,825 A | 6/1992 | Huhn | 600/529 |
| 5,178,155 A | 1/1993 | Mault | 128/718 |
| 5,179,958 A | 1/1993 | Mault | 600/531 |
| 5,214,966 A | 6/1993 | Delsing | 73/861.28 |
| 5,233,996 A | 8/1993 | Coleman et al. | 600/529 |
| 5,282,473 A | 2/1994 | Braig et al. | 600/532 |
| 5,285,794 A | 2/1994 | Lynch | 128/719 |
| 5,293,875 A | 3/1994 | Stone | 128/719 |
| 5,299,579 A | 4/1994 | Gedeon et al. | 600/532 |
| 5,303,712 A | 4/1994 | Van Duren | 600/529 |
| 5,309,921 A | 5/1994 | Kisner et al. | 600/532 |
| 5,326,973 A | 7/1994 | Eckerbom et al. | 250/343 |
| 5,355,879 A | 10/1994 | Brain | 128/207.15 |
| 5,357,972 A | 10/1994 | Norlien | 128/725 |
| 5,363,857 A | 11/1994 | Howard | 600/531 |
| 5,398,695 A | 3/1995 | Anderson et al. | 600/532 |
| 5,402,796 A | 4/1995 | Packer et al. | 128/719 |
| 5,419,326 A | 5/1995 | Harnoncourt | 128/660.02 |
| 5,425,374 A | 6/1995 | Ueda et al. | 600/532 |
| 5,450,193 A | 9/1995 | Carlsen et al. | 356/301 |
| 5,468,961 A | 11/1995 | Gradon et al. | 250/345 |
| 5,503,151 A | 4/1996 | Harnoncourt et al. | 128/660.02 |
| 5,513,648 A | 5/1996 | Jackson | 128/721 |
| 5,533,512 A | 7/1996 | Novotny et al. | 128/719 |
| 5,570,697 A | 11/1996 | Walker et al. | 128/719 |
| 5,632,281 A | 5/1997 | Rayburn | 128/719 |
| 5,645,071 A | 7/1997 | Harnoncourt et al. | 128/719 |
| 5,647,370 A | 7/1997 | Harnoncourt | 128/725 |
| 5,676,132 A | 10/1997 | Tillotson et al. | 128/204.23 |
| 5,705,735 A | 1/1998 | Acorn | 600/531 |
| 5,754,288 A | 5/1998 | Yamamoto et al. | 356/301 |
| 5,789,660 A | 8/1998 | Kofoed et al. | 73/232 |
| 5,796,009 A | 8/1998 | Delsing | 73/861.28 |
| 5,800,360 A | 9/1998 | Kisner et al. | 600/532 |
| 5,816,246 A | 10/1998 | Mirza | 128/726 |
| 5,831,175 A | 11/1998 | Fletcher-Haynes | 73/861.28 |
| 5,834,626 A | 11/1998 | DeCastro et al. | 73/23.3 |
| 5,836,300 A | 11/1998 | Mault | 600/532 |
| 5,922,610 A | 7/1999 | Alving et al. | 436/116 |
| 5,932,812 A | 8/1999 | Delsing | 73/861.02 |
| 5,957,858 A | 9/1999 | Micheels et al. | 600/532 |
| 6,010,459 A | 1/2000 | Silkoff et al. | 600/532 |
| 6,044,843 A | 4/2000 | O'Neill et al. | 128/204.23 |
| 6,099,481 A | 8/2000 | Daniels et al. | 600/538 |
| 6,135,107 A | 10/2000 | Mault | 128/204.23 |
| 6,206,837 B1 | 3/2001 | Brugnoli | 600/529 |
| 6,277,645 B1 | 8/2001 | Mault | 436/133 |
| 6,309,360 B1 | 10/2001 | Mault | 600/531 |
| 6,402,698 B1 | 6/2002 | Mault | 600/531 |
| 6,468,222 B1 | 10/2002 | Mault | 600/531 |
| 6,506,608 B2 | 1/2003 | Mault | 436/133 |
| 6,513,532 B2 | 2/2003 | Mault | 600/595 |
| 6,949,081 B1 * | 9/2005 | Chance | 604/67 |
| 6,981,947 B2 * | 1/2006 | Melker | 600/532 |
| 2003/0139681 A1 * | 7/2003 | Melker et al. | 600/532 |

* cited by examiner

A = High Physical Activity
B = Low Physical Activity

SYSTEM AND METHOD OF DETERMINING AN INDIVIDUALIZED DRUG ADMINISTRATION PROTOCOL

RELATED APPLICATION

The present application claims the benefit of U.S. Provisional Application Ser. No. 60/369,199 filed Apr. 1, 2002.

FIELD OF THE INVENTION

The present invention relates to drug administration, and more particularly to a method of determining an individualized drug administration dosage with respect to a drug to be administered to an individual, and also to a system to facilitate such a determination.

BACKGROUND OF THE INVENTION

It is well established that the effectiveness of a particular drug administered to an individual depends on factors such as the drug dosage, the frequency of the administration, or interactions with other drugs. Currently, a particular drug dosage is set forth for a predetermined body weight, and the actual dosage administered to a person is determined using the actual body weight of the person. However, this approach fails to take into account variations, other than mere body weight, which may influence the effectiveness of the drug.

For example, the effectiveness of a drug administered to an individual is influenced by the body metabolic rate of the individual, which in turn has an effect on the drug metabolic rate. An indirect calorimeter may be used in determining the resting metabolic rate (RMR) of the individual. Since the RMR varies widely among individuals, monitoring the RMR for a particular individual enables the drug administration protocol to be better optimized with respect to the particular individual. An example of an indirect calorimeter for measuring the metabolic rate of an individual is disclosed in U.S. Pat. Nos. 6,309,360; 6,402,698; 6,468,222 and 6,506,608, the disclosures of which are incorporated by reference.

In addition, a physical activity detector, such as a body-attachable detector, for detecting the physical activities of the individual, may be utilized in conjunction with the indirect calorimeter. An example of an activity monitor is disclosed in U.S. Pat. No. 6,513,532, which is hereby incorporated by reference.

It is also known that the body fat percentage of individuals varies widely, which may affect the optimum dosage amount for the particular individual.

Thus, there is a need in the art for a system and method of utilizing the metabolic rate of the individual in determining a drug dosage and frequency for a particular individual.

SUMMARY OF THE INVENTION

Accordingly, the present invention is a system and method for determining an individualized drug dosage. The system includes a metabolic rate sensing means for sensing the metabolic rate of the individual. The system also includes a computing device having a processor, a memory, an input device, and a display device. The system further includes a data storage means operatively in communication with the processor, and the data storage means includes a drug database containing drug dosage data. The method includes the steps of determining a standardized dosage for a drug. The method also includes the steps of measuring the actual metabolic rate of the individual and determining a metabolic comparison factor by comparing the measured actual metabolic rate to a predetermined standard metabolic rate. The method further includes the steps of adjusting the standardized drug dosage using the comparison factor One advantage of the present invention is that a system and method of determining an individualized drug administration protocol is provided that is tailored to the unique physiological characteristics of the individual. Another advantage of the present invention is that the metabolic rate of the individual may be determined using an indirect calorimeter and used in determining the drug administration protocol for the particular individual. Still another advantage of the present invention is that the drug administration protocol may be optimized by also monitoring the physical activity of the individual, to thereby provide an indication of the activity-related metabolic rate (AMR) of the respective individual. A further advantage of the present invention is that a system and method is provided for scaling the effective amount of the drug administered to the individual according to the actual body fat percentage of the individual. Yet a further advantage of the present invention is that a system and method is provided for preparing a personal metabolism characteristic curve for the individual, which is utilized in determining an optimum interval between drug administrations. Still a further advantage of the present invention is that a method and system of determining an individualized drug administration protocol is provided for the administration of insulin, diet-control drugs, or chemotherapy drugs to the individual.

Other features and advantages of the present invention will be readily understood as the same becomes better understood after reading the subsequent description when considered in connection with the accompanying drawings.

DESCRIPTION OF PREFERRED EMBODIMENT(S)

A drug administration protocol for a particular individual may be determined to provide optimal effectiveness of the drug. The present invention particularly takes into account the individual metabolic rate, or other factors such as the physical activity level of the individual, the actual body fat percentage of the individual relative to that of the average person, or other physical, physiological and environmental factors applicable to the particular individual, in calculating the drug dosage.

Figure 1:
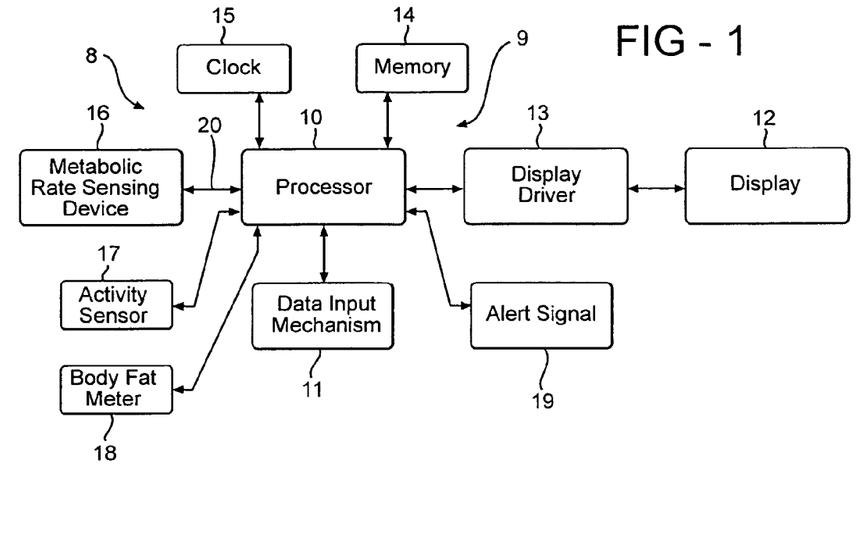
FIG. 1 is a block diagram illustrating a system for determining an individualized drug administration protocol, in accordance with the present invention.

Referring to FIG. 1, a block diagram illustrating a system 8 for determining an individualized drug dosage for a person in order to maximize the effectiveness of the drug is illustrated. The system 8 is particularly useful for administering a drug, including but not limited to insulin, diet control drugs, chemotherapy drugs, or other such drugs in which it is desirable to maximize the effectiveness of the drug.

The system 8 includes a computing device 9 for determining the drug dosage. The computing device includes a processor 10. The processor 10 is of a general-purpose or dedicated-purpose construction, and includes a conventional data input mechanism or device 11 and a display device 12 driven by a display driver 13. The processor 10 further includes a data storage means 14 and a clock 15, as well as other components (not shown) conventionally used in computers or other such data processors. In this example, the data storage means 14 is a memory. Various types of information may be stored in the data storage device. For example, a database of different types of drugs may be stored in the database, and for each drug, the drug dosage information is provided. This information may be in the form of a standardized drug dosage for an average individual within a predetermined average weight range.

The system 8 includes a metabolic rate sensing device 16 for measuring the metabolic rate of a person. The processor 10 receives the input from the metabolic rate sensing device 16, for measuring the metabolic rate of the patient. The device 16 is operatively in communication with the processor 10 and provides metabolic rate data to the processor 10. The processor 10 uses the metabolic rate data in calculating the drug dosage. One example of such a device 16 is an indirect calorimeter. Examples of an indirect calorimeter are disclosed in U.S. Pat. Nos. 4,917,108; 5,038,792; 5,178,155; 5,179,958; and 5,836,300, all to Mault, an inventor of the present application, which are incorporated herein by reference. These patents disclose systems for measuring metabolism and related respiratory parameters through indirect calorimetry. These instruments generally employ flow meters which pass both the inhalations and the exhalations of a user breathing through the instrument and integrate the resulting instantaneous flow signals to determine total full flow volumes. In some embodiments, the exhaled gases generated by the user are passed through a carbon dioxide scrubber before passing through the flow meter so that the differences between the inhaled and exhaled volumes is essentially a measurement of the oxygen consumed by the lungs. In other embodiments, the concentration of carbon dioxide exhaled by the user is determined by passing the exhaled volume through a capnometer and integrating that signal with the exhaled flow volume. The oxygen consumption can then be calculated as the difference between the inhaled and exhaled oxygen volumes, corrected to standard conditions.

Recently, James R. Mault, M.D. and others invented an improved indirect calorimeter, more fully described in U.S. Pat. Nos. 6,309,360; 6,402,698; 6,468,222 and 6,506,608, the contents of which are incorporated herein by reference. The improved calorimeter includes an ultrasonic detection apparatus combined with an oxygen sensor. This improved calorimeter can be adapted for use in a variety of situations, such as with an intubated patient, or other patient connected in some manner to a mechanical ventilator or respirator.

The oxygen consumption of a person is related to their resting metabolic rate (RMR). This can increase up to several hundred percent due to certain medical conditions, including trauma victims or burn patients. In addition, the nutritional requirements of a person are also determined by their metabolic rate. An enhanced RMR can lead to muscle wasting of a patient, as muscle burning proceeds in order to supply the person with the required additional energy. Hence, for optimized recovery of a patient, it would be valuable to know their metabolic rate. In addition, the correct ventilation of a patient requires knowledge of carbon dioxide and oxygen levels in the blood. The carbon dioxide and oxygen levels in arterial blood can be determined using the end tidal gas component concentrations of exhaled breath.

The metabolic rate device 16 can be utilized to measure the actual metabolic rate of the individual during a predetermined condition, such as at rest, while engaged in normal activities, or while exercising or the like. The actual metabolic rate can be compared to that of the average person, and used in determining the individualized drug dosage, including the amount and/or frequency interval. Since such physical activities can vary widely among individuals, preferably the metabolic rate meter 16 measures the actual resting metabolic rate of the individual.

The system 8 may also receive input information from other sensors, such as an activity sensor 17. As will be described more particularly below, these inputs may also be used in determining the drug dosage for a particular individual according to the specific physiological characteristics of the individual. Other factors affecting such a determination may also be provided as an input, such as age, sex, ethnic characteristics, and ambient conditions of temperature, altitude, and pressure. In addition, medical condition factors may further be provided as an input, such as sleep/wake state or trauma state of the individual, use of medical devices such as ventilators by the individual, the intake of other drugs, or other factors applicable to the particular individual which may affect the drug administration protocol for maximum effectiveness. It is foreseeable that these factors may be manually input into the processor by the data input mechanism 11, or automatically by sensors which sense the respective conditions.

When the individual is engaged in normal activities, the system may include an activity sensor 17 for measuring the actual activities of the individual for use in determining the drug administration protocol for the respective individual.

Activity sensor 17 may be any one of many known types of such sensors, e.g., one attachable to the body of the individual so as to sense all motions of the individual. The activity level signal from activity sensor 17 may be correlated with one or more other factors influencing the actual level of physical activities, such as vertical acceleration of the person's torso (e.g., when running uphill or downhill), heartbeat, speed of running or walking, distance traveled, or other physiological condition affecting the drug metabolic rate as a result of physical activity.

The processor may further receive input information from a body fat meter 18. Various devices are known in the art for actually measuring the body fat percentage of the individual. The body fat meter 18 may be based on established principles such as buoyancy, body dynamics, spectroscopic methods, bioimpedance, or other methods known in the art for measuring the body fat percentage of the individual. For example, Tanita of Japan manufactures various body weight scales including a four electrode bioimpedance system for the calculation of body fat percentage. The person's height can be entered or otherwise determined to assist calculation of body fat percentage.

The system 10 is also provided with a conventional output display 12. The output display 12 can be used for displaying information, such as the individualized drug dosage, as determined by the processor 10, as will be described more particularly below.

The system 8 may also include an alert signal 19 operatively in communication with the processor that can be used for alerting the individual when the drug is to be administered, or other such action to be taken. It should be appreciated that the alert signal device may be deactivated, such as when the patient is asleep.

The system 8 of FIG. 1 may be incorporated in a unitary device. Alternatively, the metabolic rate sensing device 16 is a separate device that is operatively in communication with the computing device 9 via a communications link 20. Various types of communications links are contemplated, such as a wired or a wireless connection. One example of a wireless link is a universal short-wave wireless connectivity protocol, such as Bluetooth. Another example of a wireless link is a memory module. Still another example is the Internet or an intranet. In this example, the computing device is a portable computing device, such as a notebook computer, a handheld computer, a palm held organizer, a personal digital assistant, a web enabled cellular phone or the like that provides computing and information storage and retrieval. Alternatively, a personal computer may be used to receive, process and transmit the data.

Figure 2A:
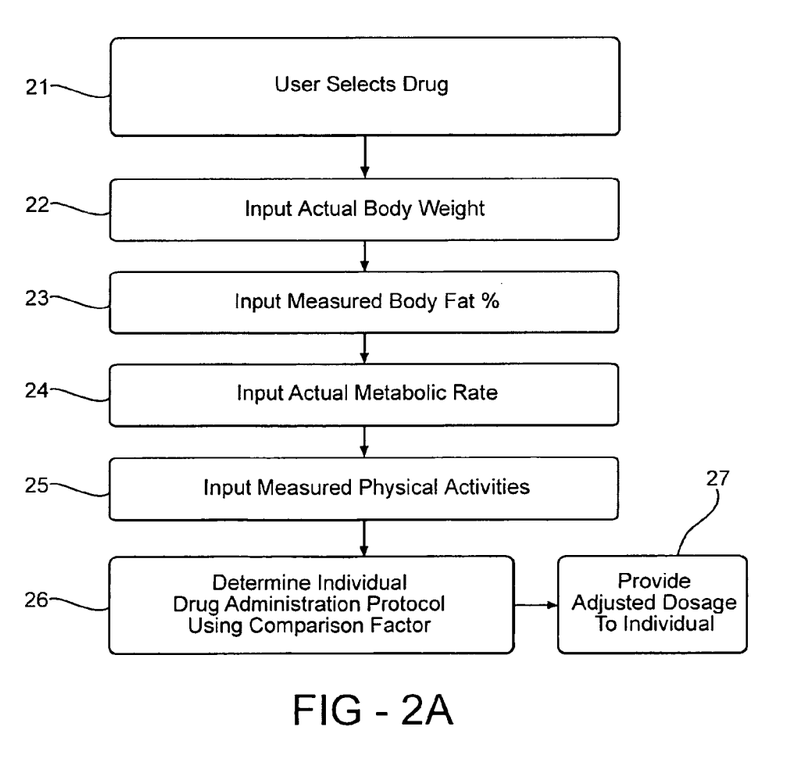
FIGS. 2a-2c are flowcharts illustrating a method of determining an individualized drug administration protocol using the system of FIG. 1, according to the present invention.
Figure 2B:
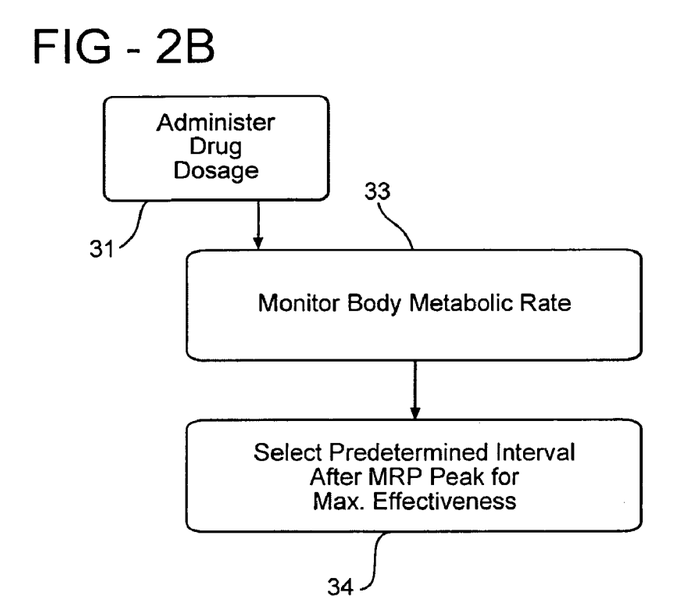
Figure 2C:
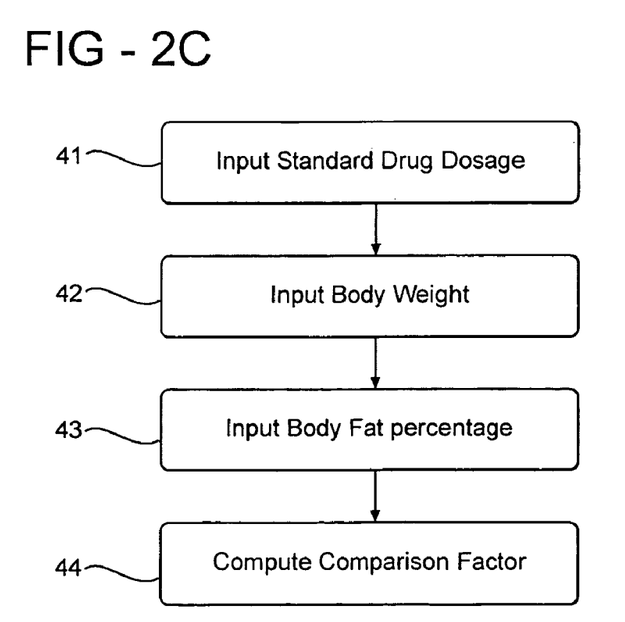

Referring to FIGS. 2a-2c, a method for determining an individualized drug dosage is provided using the system of FIG. 1. The method is preferably implemented by a software program resident in the processor 10 of the computing device 9.

The methodology begins in block 21 and a user selects a drug, preferably from a database of drugs stored in the data storage device 14. In this example, the user is a medical professional. The database includes information regarding a particular drug, including a summary of drug characteristics, such as predetermined standard dosage amount and dosage frequency for a predetermined condition. The database may also include a standard resting metabolic rate for a predetermined body type. The standard resting metabolic rate may be found for the average body weight, assuming an average body fat percentage, lean body weight, frame size, or other build-related factor.

The methodology advances to block 22 and the actual body weight of the individual is provided as an input to the system 8 using the input device 11. This measurement may be provided as an input by the user using the input device 11, or it may be sensed using a scale, and a signal corresponding to the sensed body weight is communicated to the processor 10.

The actual body weight of the individual is utilized to select the predetermined standard drug dosage. The predetermined standard dosage amount is associated with a predetermined weight range. The predetermined standard dosage amount also reflects the frequency of administering the drug to an individual within a given weight range. In the past, the amount of the drug administered to the individual was based on the individual's weight. The methodology advances to block 23.

In block 23, a body fat measurement of the individual may be provided as an input to the system 9. The body fat measurement may be directly entered by the user using the input device 11. Alternatively, the measured body fat of the individual can be supplied by the individual, or sensed by the body fat meter 18. This measurement may be another factor in determining an individual drug administration protocol for the particular individual.

For example, the lean body weight of a person may be calculated by subtracting the body fat percentage of body weight from the total body weight. The drug dose can then be adjusted using the lean body weight, such that the drug dose would be proportional to the lean body weight. The methodology advances to block 24.

In block 24, the actual metabolic rate of the individual is measured and provided as an input to the processor 10. The metabolic rate is preferably directly measured as previously described using an indirect calorimeter and transmitted to the processor 10. The metabolic rate may be measured at rest, or while the patient is engaged in an activity. The metabolic rate is entered directly by the user using the input mechanism, or sensed using the metabolic rate sensing device 16 and transmitted to the processor 10 via the communications link 20. The methodology advances to block 25.

In block 25, the physical activity of the patient may be provided as an input to the processor 10. It should be appreciated that the drug may be metabolized at a faster rate if the individual is engaged in a physical activity. The physical activity may be sensed using the activity sensor 17 as previously described, or input manually using a data input mechanism 11. For example, if the predetermined standard drug dosage information for the average person is based on an average actual body metabolic rate while at rest, the metabolic rate device 16 may be used for measuring the actual resting body metabolic rate of the individual. On the other hand, if the predetermined standard drug dose information for the average person was based on an active metabolic rate, the device 16 could be used for measuring the active metabolic rate of the individual, and activity sensor 17 could be used for measuring the actual physical activities of the individual to determine an activity related energy expenditure. Data processor 10 thus receives inputs from both metabolic rate sensing device 16 and activity sensor 17 to provide information for use in computing the actual metabolic rate of the individual.

The methodology advances to block 26 and determines an individual drug dosage, also referred to as an administration protocol, for the respective person. The actual metabolic rate of the individual is compared to the predetermined standard metabolic rate stored in the database for the drug, and a comparison factor is established. As previously described, the actual resting metabolic rate or actual activity related metabolic rate may be utilized. The comparison factor is the ratio of the actual metabolic rate and the average metabolic rate. Similarly, the comparison factor could be the difference.

The drug dosage is determined using the standard drug dosage and the comparison factor. For example, if the standard RMR was 3000 Kcal/day, and the actual RMR 2000 Kcal/day, the comparison factor using the ratio method would be 2/3. For a standard dosage of 30 mg, the individualized dosage would be (30 mg) (2/3) or 20 mg. Thus, if a patient's resting metabolic rate is 90% of the predetermined standard RMR, they are administered 90% of the standard dosage. The standard RMR assumes an average build and body fat percentage for a predetermined weight. Other factors may include age, ethnic background, medical condition, other drugs, ambient conditions, sleep state, the use of medical devices or other such factors. Alternatively, if the predetermined standard dosage for the individual was 500 mg of the drug to be taken each eight hours, the comparison factor is used to adjust the predetermined standard dosage amount (e.g., 500 mg to 400 mg) and the dosage frequency (e.g., from eight hours to seven hours), in order to maximize the effectiveness of the drug.

The drug dosage may be further modified using another factor, to account for another physical or physiological parameter. For example, if the person engages in an activity, the signal from the activity sensor 17 is utilized to determine an activity related energy expenditure. The activity related energy expenditure and actual active metabolic rate measurement are compared to the standard metabolic rate to determine a comparison factor. The dosage, including quantity and frequency, is adjusted. For example, the dosage may be increased and/or the frequency in a manner that correlates with the individual's activity level.

Alternatively, the individual is reminded at intervals to take a dose of the drug. The intervals will be a certain time period if no activity is detected by the activity sensor, and this time period is modified if activity levels are determined. For example, the time period may be reduced by a factor proportional to, or otherwise correlated with, the activity level. The time period is determined by the processor, which can receive signals from the clock, accesses data stored in the memory, and receives data input from the input mechanism. During the person's known sleeping or resting periods, the alert can be disabled.

If the person engages in activity, the time period is reduced in a manner correlated with the activity signal level from the activity sensor and one or more factors stored in the memory. The activity signal level can be correlated with vertical acceleration of the person's torso, heartbeat (or other physiological indication of activity), physical location (for example, speed during running as determined from a global positioning sensor), or other factor.

The methodology advances to block 27 and adjusted drug dosage is provided to the user. For example, the optimum drug dosage may displayed on the display screen 12.

It will also be appreciated that the adjusted dosage may be determined using one or more of the aforementioned inputs besides resting metabolic rate, including body weight, body fat and physical activity based on all the foregoing factors.

Referring to FIG. 2b, a flowchart of an other embodiment of a method of monitoring the metabolic rate of a person over time after the drug is administered is illustrated.

As previously described, the drug administration protocol for a particular individual to provide maximum effectiveness depends not only on the actual weight of the individual compared to the average weight used for determining the standard drug administration conditions, but also on other factors. The present invention particularly takes into account factors such as the body metabolic rate, the physical activity level of the individual, or the actual body fat percentage of the individual relative to that of the average person, among other physical, physiological and environmental factors applicable to the particular individual.

The rate that an administered drug is metabolized by the individual affects the effectiveness of the drug. The drug metabolic rate may be determined by monitoring the metabolic rate of the individual after an amount of the drug has been administered. This is schematically illustrated in FIG. 3.

According to this embodiment of the present invention, a metabolism characteristic curve is produced for the respective individual by administering to the individual a predetermined dosage of the drug, and monitoring the body metabolic rate of the individual both before and after the administration of the drug. Since the drug metabolic rate, and thereby the drug effectiveness, generally corresponds to the body metabolic rate, such a characteristic curve will provide an indication of the changes with time in the effectiveness of the drug. For example, a weight loss program may include the administration of a metabolic rate enhancing drug.

One or more characteristic times related to the time dependence of the metabolic rate are then determinable. These characteristic times can then be used in determining the dynamics of the drug activity, and thereby improve the dosage mechanisms. Thus, a dose can be administered at an interval, where the interval is correlated with the influence of the drug on the metabolic rate of the user. For example, the drug may be administered at the time where the effectiveness level returns to a predetermined level, such as the initial baseline level.

Figure 3:
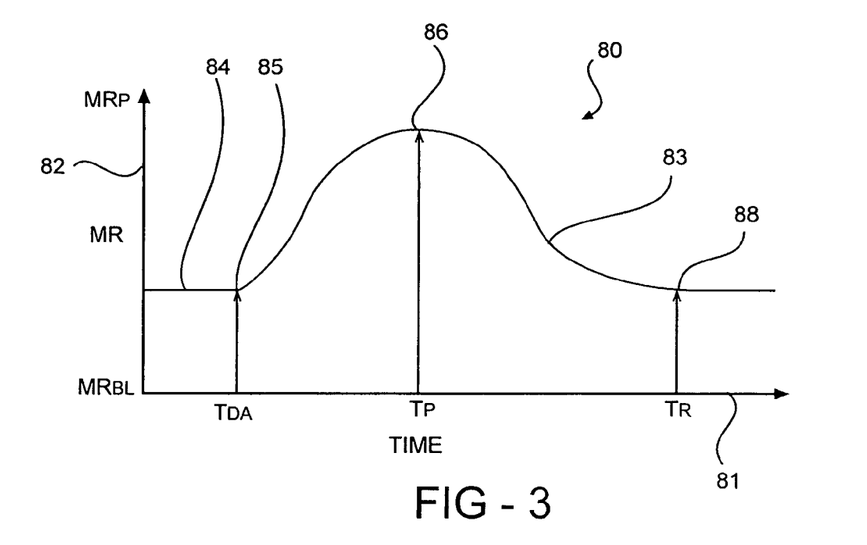
FIG. 3 is a graph illustrating the variation in the metabolic rate of the individual after having received a drug using the system of FIG. 1 and the method of FIGS. 2a-2c according to the present invention.
Figure 4:
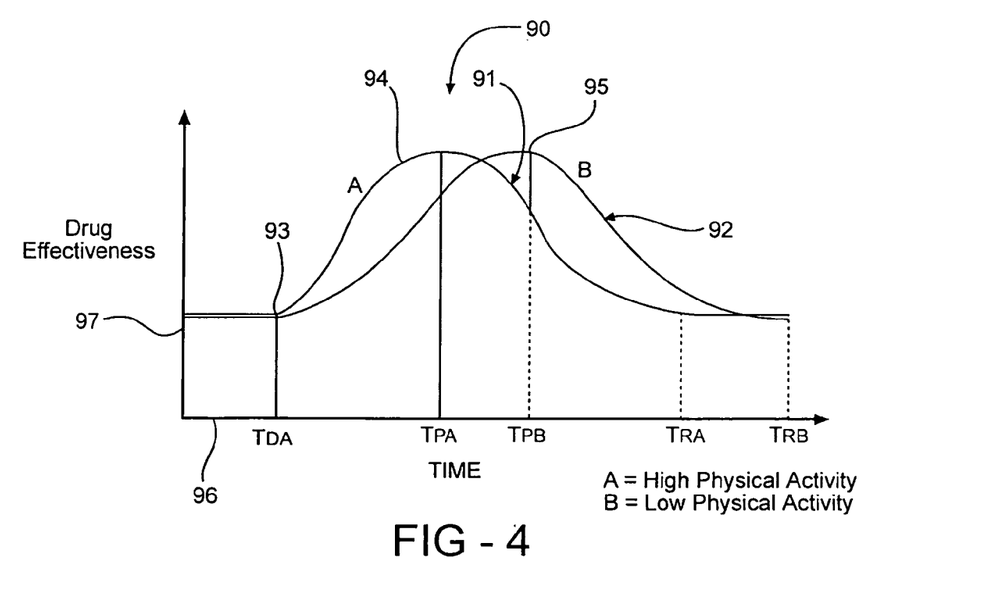
FIG. 4 is a graph illustrating a variation in the effectiveness of the drug over time for different levels of physical activity according to the present invention.

A metabolism characteristic curve, such as the curve shown in FIG. 3, may be determined for the particular individual and the particular drug. Using such a personal characteristic curve, an optimum time between doses of the drugs can then be determined. It should be appreciated that the individual can be alerted to take the drug at an interval correlating with a characteristic time of the metabolic response curve.

The methodology begins in block 31, and a drug dosage is administered to the patient. It should be appreciated that the drug dosage may be a standard drug dosage based on average person, or it may be the individualized drug dosage determined using the methodology described with respect to FIG. 2a. The methodology advances to block 33.

In block 33, the metabolic rate of the individual is monitored over time. Referring to FIG. 3, the metabolic rate of an individual over time due to a drug is illustrated at 80. The x-axis represents time, as shown at 81, and the y-axis represents the metabolic rate, as shown at 82. The rate of change over time of the patient's metabolic rate is shown at 83. For an individual patient, such a curve may be used in determining the optimum time interval between administrations of the drug for maximum effectiveness.

In this example, before the drug is administered, the metabolic rate of the patient prior to administering the drug is a baseline level, shown at 84. The drug is administered at a point in time, as shown at 85. In this example, the metabolism of the patient increases, with a metabolic rate maximum at a time, as shown at 86. A peak time $T_p$ may be defined as the difference between the time of drug administration 85 and the peak of metabolic rate, as shown at 86. The metabolic rate of the patient subsequently falls to the resting level at a time shown at 88.

The peak time 86 is one of several characteristics that can be used to characterize the curve 80. Other characteristics include the rise times in terms of exponentials or other factors, decay times and numerical modeling factors.

The characteristic times may be used in determining the dynamics of the drug activity, and improved dosage mechanisms. For example, a dosage can be administered at intervals, and the intervals may be correlated with the characteristic time determined. In this example, the peak drug metabolic rate ($MR_p$) in such a curve, which indicates the peak in the drug effectiveness, can be used for determining the optimum time for administering the next drug dosage in order to achieve maximum effectiveness for the respective patient. For example, in some drugs it may be desirable to administer the next dosage as soon as the drug effectiveness drops from the peak to the baseline level, whereas in other cases it may be desirable to administer the next dosage at a predetermined point before the effectiveness drops to the baseline level, or at a predetermined point after the effectiveness drops to the baseline level.

Referring to FIG. 2c a flowchart illustrating still another embodiment of the present invention using a body fat meter is provided. The system 8 includes a body fat meter 18, such as the previously described body fat meter 18 for measuring a body fat percentage. Such a system could include a weighing mechanism and a data processor adapted to calculate an optimum drug dosage for an individual in terms of the lean body weight of the individual and the identity of the drug.

The methodology begins in block 41, and a standard drug dosage is provided as an input to the processor for the respective drug, as previously described. The methodology advances to block 42, and the body weight of the respective patient is provided as an input to the processor, as previously described.

The methodology advances to block 43, and the body fat percentage of the respective patient is then measured and provided as an input to the processor. The methodology advances to block 44.

In block 44, the methodology determines a comparison factor, using the methodology described with respect to FIG. 2a, taking into consideration the body weight and body fat percentage of the respective individual. The comparison factor is utilized to adjust the standard dosage for the individual. Thus, the body fat percentage is utilized in determining the comparison factor for scaling the average drug dosage, as previously described. The methodology continues as described with respect to FIG. 2a.

As indicated earlier, the foregoing system and method are particularly useful for determining an optimum drug administration protocol with respect to various types of drugs in which it may be critical, or highly desirable, to optimize the drug dosage amount, and/or the drug administration interval, to maximize the effectiveness of the drug.

In addition, as described above with respect to FIG. 3, an effective amount of the drug may be administered to the individual, and the metabolic rate of the individual may be monitored to produce a metabolism characteristic curve. The metabolism characteristic curve corresponds to the changes over time of the body metabolic rate of the patient, which correlate with the changes over time of the drug metabolic rate. This curve also demonstrates the change in the drug effectiveness for the patient, and it thereby may be utilized for determining the optimum drug administration protocol for the respective patient.

It is generally understood that a drug is metabolized at a faster rate if the person is engaged in physical activity. Therefore, a medical professional may decide to increase the dosage, or adjust the time period between doses, in a manner that correlates with the level of the person's activity.

Figure 5:
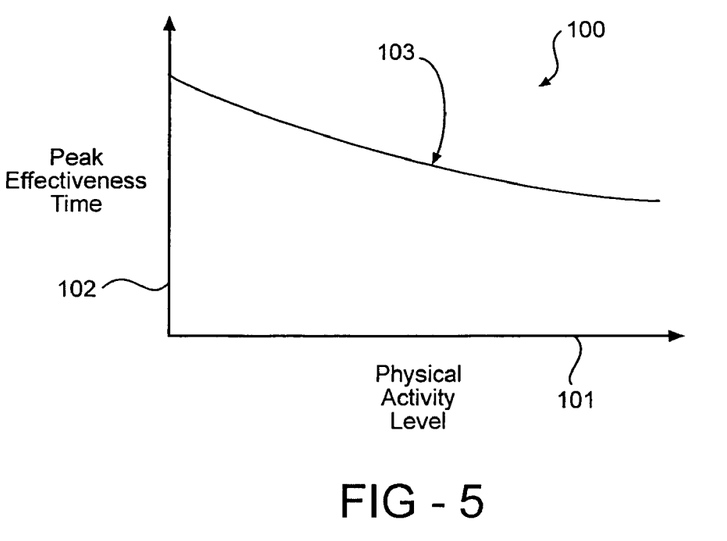
FIG. 5 is a graph illustrating a variation in peak drug effectiveness due to different physical activity levels, according to the present invention.

The physical activity level of a person can also be included in the dynamic model of drug effectiveness represented by the personal metabolism characteristic curve. FIG. 5 illustrates drug effectiveness as a function of time for two different levels of physical activity as shown at 90.

The x-axis shown at 96 represents time, and the y-axis shown at 97 represents drug effectiveness. In FIG. 5, curve A shown at 91 corresponds to a higher physical activity level than curve B shown at 92, so that the drug is metabolized faster. A peak time for drug effectiveness (or peak effectiveness time) can be defined as the time between the drug administration ($T_{DA}$) shown at 93 and the time of peak effectiveness ($T_{PA}$ shown at 94, and $T_{PB}$ shown at 95, respectively). The peak effectiveness times $T_{PA}$, $T_{PB}$ are physical activity level dependent, a factor not included in conventional drug administration methods. As indicated above, other characteristic times of drug metabolism can be used.

Figure 6:
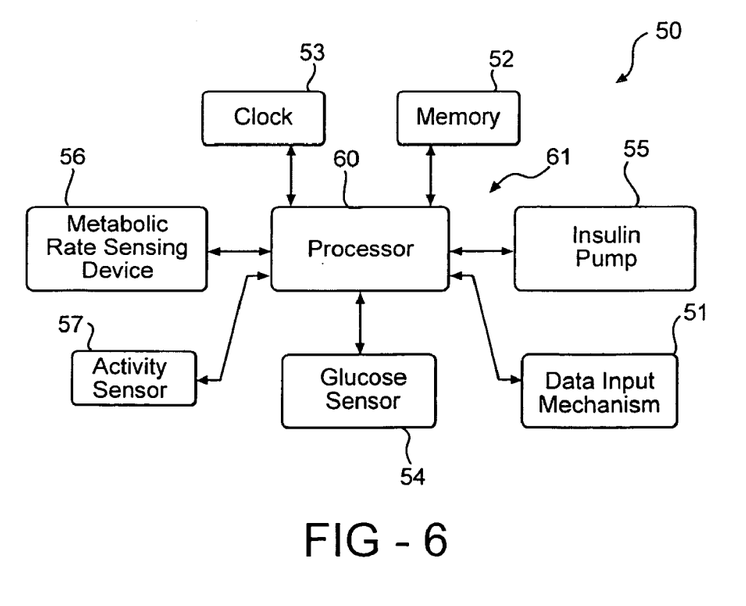
FIG. 6 is a block diagram illustrating the application of the system of FIG. 1 for controlling a drug delivery device according to the present invention.

In FIG. 6, how peak effectiveness time varies with the activity level of the individual is illustrated at 100. The x-axis represents physical activity level, shown at 101. The y-axis represents peak effectiveness time shown at 102. The change in peak effectiveness time for changes in activity level is shown at 103. Hence, by determining activity levels of a person over time, the optimum time between drug doses may be determined. For example, an average activity level over a time period since the last dosage of a drug may be computed so as to determine whether the time for a subsequent dose has arrived. An average activity level can be used to determine a peak effectiveness time. Alternatively, a parameter correlated with the drug metabolic rate can be computed over time, correlated with the activity level; and the parameter then integrated. When the integrated parameter reaches a certain threshold, the person can be alerted to take another drug dose.

Referring to FIG. 6, a further embodiment of the present invention is provided for maximizing the effectiveness of a drug delivery therapy through injection or controlled drug infusion. With this technique, a drug delivery device, such as a constant delivery implantable pump, is utilized to deliver a predetermined amount of a drug to a patient in a predetermined manner. In this example, the drug is insulin administered to a diabetic. The system 50 is particularly useful for diabetic patients, in order to control an insulin pump to administer insulin automatically at the proper times.

The system 50 includes a computing device 61 having a processor 60, a data input mechanism 51, a memory 52, and a clock 53, corresponding in function to the similar devices described above with respect to FIG. 1. The computing device 61 also receives an input from a glucose sensor 54, which senses the actual blood glucose level and which controls, via processor 60, an insulin pump 55 for delivering the insulin to the patient.

It is anticipated that such a system 50 may also provide an alert signal indicating a predetermined condition, via a signaling device 19. For example, the alert signal may indicate that it is time for the patient to receive an insulin-injection, or that a critical situation has arisen due to a failure to take an insulin injection at the proper time.

In accordance with the present invention, however, the computing device 61 also receives an input from a metabolic rate sensing device 56, and/or from an activity sensor 57, corresponding to metabolic rate sensing device 16 and activity sensor 17 described with respect to the system of FIG. 1, for continuously monitoring the metabolic rate and/or the physical activities of the user and for controlling the insulin pump 55 in response thereto. For example, if the metabolic rate of the user increases, and/or the physical activity of the user increases, the processor 60 would control the insulin pump 55 to administer more insulin at a predetermined interval, in order to optimize the administration of the insulin according to the existing conditions of the user. On the other hand, if the metabolic rate of the user decreases, and/or the physical activity level decreases, the insulin pump 55 would be controlled to decrease the amount of insulin administered and to adjust the interval between the administration of the insulin accordingly.

The data input mechanism 51 is adapted to receive additional data, e.g., from user inputs or additional sensors. Data input mechanism 51 may also receive dietary data, e.g., from a diet calculator or PDA used to record food consumption. It is contemplated that the data input mechanism 51 may be a keypad, data port, wireless transceiver, or the like.

The computer device 61 is preferably contained within a housing, and the device may be mounted on the body of the person. It is also contemplated that the blood glucose meter may be a unitary device. Alternatively, the blood glucose sensor 54 may be a separate unit, transmitting data to the computing device 61 by a suitable communications link, such as a wireless transmission mechanism, cable, optical link, or the like.

While the invention has been described with respect to several preferred embodiments, it will be appreciated that these are set forth merely for purposes of example, and that many other variations and applications of the invention may be made.

What is claimed is:

1. A method of determining an individualized drug dosage for an individual, said method comprising the steps of:
    determining a standardized dosage for a drug;
    measuring the actual metabolic rate of the individual through use of an indirect calorimeter to analyze the composition of inhalation and exhalation respiratory gases of the individual;
    determining a metabolic comparison factor by comparing the measured actual metabolic rate to a predetermined standard metabolic rate; and
    adjusting the standardized drug dosage using the comparison factor.

2. The method according to claim 1, wherein the metabolic rate of the individual is measured while the individual is resting.

3. The method according to claim 1, wherein the metabolic rate is measured while the individual is engaged in a physical activity.

4. The method according to claim 1, wherein the standardized drug dosage is based on average body weight.

5. The method according to claim 1 further including the step of administering the adjusted drug dosage to the individual.

6. The method according to claim 1, wherein the adjusted drug dosage includes an amount of the drug relative to a period of time.

7. The method according to claim 1, wherein said step of determining a standardized drug dosage further includes the steps of:
    selecting the standardized drug dosage from a drug database containing drug dosage information that is stored in a drug storage means in communication with a computing device having a processor, an input device, a memory and a display device.

8. The method according to claim 7, further including the steps of: communicating an actual body weight to the computing device; and communicating the actual metabolic rate to the computing device, wherein the computing device is used to determine the adjusted drug dosage.

9. The method according to claim 7, further including the steps of:
    sensing the activity level of the individual using a body activity monitoring means;
    transmitting the sensed activity level to the processor;
    measuring the active metabolic rate of the individual; and
    using the measured active metabolic rate and activity level in determining the metabolic correction factor.

10. The method according to claim 7, further including the steps of:
    sensing a body fat level of the individual using a body fat sensing means;
    transmitting the sensed body fat level to the processor; and
    using the sensed body fat level in determining the comparison factor.

11. The method according to claim 7, further including the step of alerting the individual when to receive the drug using a signaling means operatively in communication with the computing device.

12. The method according to claim 1, further including the steps of:
    administering the drug to the individual;
    monitoring the change in metabolic rate of the individual over time as the drug is metabolized; and
    using the change in metabolic rate in determining a comparison factor for adjusting drug dosage.

13. A method of determining an individualized drug administration protocol for an individual, comprising:
    selecting a drug to administer to the individual, wherein the drug is selected from a drug database containing drug dosage information that is stored in a drug storage means in communication with a computing device having a processor, an input device, a memory and a display device;
    communicating an actual body weight of the individual to the computing device; measuring the actual metabolic rate of the individual;
    using an indirect calorimeter to measure an actual metabolic rate by analyzing the composition of inhalation and exhalation respiratory gases of the individual;
    communicating the actual metabolic rate of the individual to the computing device;
    determining a comparison factor by comparing the measured actual metabolic rate to a predetermined standard metabolic rate; and
    adjusting a predetermined drug dosage for the drug using the comparison factor.

14. The method according to claim 13, further including the step of administering the adjusted drug dosage to the individual.

15. The method according to claim 14, wherein the metabolic rate of the individual is measured while the individual is resting.

16. The method according to claim 14, wherein said metabolic rate is measured while the individual is engaged in a physical activity.

17. The method according to claim 13, further including the steps of:
    sensing the activity level of the individual using a body activity monitoring means;
    transmitting the sensed activity level to the processor;
    measuring the active metabolic rate of the individual; and
    using the measured active metabolic rate and activity level in determining the correlation factor.

18. The method according to claim 13, further including the steps of:
    sensing a body fat level of the individual using a body fat sensing means;
    transmitting the sensed body fat level to the processor; and
    using the sensed body fat level in determining the comparison factor.

19. The method according to claim 13, wherein the drug is administered to the individual using a drug delivery device.

20. The method according to claim 13, further includes the step of alerting the individual when to receive the drug using a signaling means operatively in communication with the computing device.

21. The method according to claim 13, further including the steps
- administering the drug to the individual;
- monitoring the change in metabolic rate of the individual over time wherein the metabolic rate changes over time as the drug is metabolized; and
- using the change in metabolic rate in determining a comparison factor for adjusting the drug dosage.

22. The method according to claim 21, wherein the drug dosage includes a dosage measured from a time of administering the drug to a time of peak metabolic rate.

23. A system for determining in individualized drug dosage for an individual, comprising:
- a metabolic rate sensing means for sensing the metabolic rate of the individual;
- a computing device having a processor, a memory, an input device, and a display device;
- a data storage means operatively in communication with said processor, wherein said data storage means includes a drug database containing drug dosage data;
- a body fat sensing means for sensing a body fat percentage of the individual, wherein a signal indicative of the sensed body fat is transmitted to the processor via a communications link;
- wherein said processor utilizes said sensed metabolic rate and said sensed body fat in determining a comparison factor, and said processor utilizes the comparison factor to adjust a standard dosage of the drug for the individual.

24. The system according to claim 23, wherein said metabolic rate sensing means is an indirect calorimeter for analyzing the composition of inhalation and exhalation gases of the individual and for producing an output corresponding thereto.

25. The system according to claim 23, further comprising a physical activity sensing means for detecting a physical activity of the individual for use in determining the comparison factor, wherein a signal indicative of the sensed activity level is transmitted to the computing device via a communications link.

26. The system according to claim 23, further comprising:
a drug delivery means for administering the drug to the individual.

27. The system according to claim 23, further comprising:
an alert device actuated by said processing means for alerting when to administer the drug dosage.

28. The system according to claim 23 wherein the standard metabolic rate is based on an average person of average body weight, height and body fat percentage.

29. The system according to claim 23 wherein the standard drug dosage is determined for an average person of average body weight and average metabolic rate.

30. The system according to claim 23 wherein the computing device is a personal handheld computer.

31. The system according to claim 23 wherein the computing device and the metabolic rate sensing means are contained within a housing.

* * * * *